(12) United States Patent
Liversidge et al.

(10) Patent No.: US 6,221,400 B1
(45) Date of Patent: Apr. 24, 2001

(54) METHODS OF TREATING MAMMALS USING NANOCRYSTALLINE FORMULATIONS OF HUMAN IMMUNODEFICIENCY VIRUS (HIV) PROTEASE INHIBITORS

(75) Inventors: Gary G. Liversidge, West Chester; David A. Engers, Collegeville; Mary E. Roberts, Downingtown; Stephen B. Ruddy, Schwenksville; Sui-Ming Wong, Collegeville; Shuqian Xu, Phoenixville, all of PA (US)

(73) Assignee: Elan Pharma International Limited, Shannon (IE)

( * ) Notice: Subject to any disclaimer, the term of this patent is extended or adjusted under 35 U.S.C. 154(b) by 0 days.

(21) Appl. No.: 09/225,498

(22) Filed: Jan. 6, 1999

Related U.S. Application Data

(60) Division of application No. 08/890,602, filed on Jul. 9, 1997, now Pat. No. 6,045,829, which is a continuation-in-part of application No. 08/800,006, filed on Feb. 13, 1997, now abandoned.

(51) Int. Cl.$^7$ .................................................... A61K 9/14
(52) U.S. Cl. ........................................... 424/489; 424/494
(58) Field of Search ................................... 424/405, 484, 424/490, 494, 489

(56) References Cited

U.S. PATENT DOCUMENTS

| | | |
|---|---|---|
| 5,145,684 | 9/1992 | Liversidge et al. . |
| 5,399,363 | 3/1995 | Liversidge et al. . |
| 5,429,824 | 7/1995 | June . |
| 5,518,187 | 5/1996 | Bruno et al. . |
| 5,518,738 | 5/1996 | Eickhoff et al. . |
| 5,559,158 * | 9/1996 | Al-Razzak . |
| 5,622,938 | 4/1997 | Wong . |
| 6,045,829 * | 4/2000 | Liversidge et al. . |
| 6,068,858 * | 5/2000 | Liversidge et al. . |

FOREIGN PATENT DOCUMENTS

| | | |
|---|---|---|
| 98/47492 | 10/1998 | (WO) . |
| 98/57648 | 12/1998 | (WO) . |

OTHER PUBLICATIONS

Chaturvedi et al., *Chemical Abstracts*, vol. 130, #71577, 1998.*

"The Protease Inhibitors Backgrounder," Office of Special Health Issues and Division of Antiviral Drug Products, Food and Drug Administration (Dec. 4, 1998).

*Physicians' Desk Reference* 53$^{rd}$ Edition, "Invirase™; saquinavir mesylate," pp. 2685–2688 (Medical Economics Co., 1999).

*Physicians' Dest Reference*, 53$^{rd}$ Edition, "Fortovase™; saquinavir," pp. 2675–2681 (Medical Economics Co., 1999).

*Physicians' Dest Reference* 53$^{rd}$ Edition, "Novir™; ritonavir," 464–469 (Medical Economics Co., 1999).

*Physicians' Dest Reference*, 53$^{rd}$ Edition, "Viracept®; nelfinavir," 484–487 (Medical Economics Co., 1999).

M. Markowitz, "Protease Inhibitors" pp. 2,7 (International Association of Physicians in AIDS Care, Sep. 1997).

*Physicians' Dest Reference*, 53$^{rd}$ Edition, "Crixivan®; indinavir," 1762–1766 (Medical Economics Co., 1999).

* cited by examiner

*Primary Examiner*—Raj Bawa
(74) *Attorney, Agent, or Firm*—Foley & Lardner

(57) ABSTRACT

The present invention describes formulations of nanoparticulate HIV protease inhibitors comprising a cellulosic surface stabilizer. The nanoparticulate formulations have an increased rate of dissolution in vitro, an increased rate of absorption in vivo, a decreased fed/fasted ratio variability, and a decreased variability in absorption. The present invention is also directed to methods of making the novel formulations. In particular, nanoparticulate formulations of HIV type 1 (HIV-1) and type 2 (HIV-2) protease inhibitors are described.

13 Claims, No Drawings

METHODS OF TREATING MAMMALS USING NANOCRYSTALLINE FORMULATIONS OF HUMAN IMMUNODEFICIENCY VIRUS (HIV) PROTEASE INHIBITORS

CROSS-REFERENCE TO RELATED APPLICATION

This application is a divisional application of Ser. No. 08/890,602, filed on Jul. 9, 1997, now U.S. Pat. No. 6,045,829, which is a continuation-in-part application of Ser. No. 08/800,006, filed on Feb. 13, 1997, now abandoned, the disclosure of which is specifically incorporated by reference.

BACKGROUND OF THE INVENTION

1. Field of the Invention

The present invention relates to formulations of nanoparticulate human immunodeficiency virus (HIV) protease inhibitor drug substances comprising a cellulosic surface stabilizer. The nanoparticulate formulations have an increased rate of dissolution in vitro, an increased rate of absorption in vivo, a decreased fed/fasted ratio variability, and a decreased variability in absorption. The present invention is also directed to methods of making the novel formulations. In particular, nanoparticulate formulations of HIV type 1 (HIV-1) and type 2 (HIV-2) protease inhibitors employing cellulosic stabilizers are disclosed.

2. Description of the Related Art

It is known that with an increase in surface area of a particulate therapeutic agent, the rate of dissolution of the agent increases. Such an increase in surface area can be obtained by decreasing the particle size of the agent. Increasing the rate of dissolution of a therapeutic agent is often desirable because it can result in an increased rate of absorption in vivo, increased bioavailability, and decreased variability in absorption of the agent.

Bioavailability is the degree to which a drug becomes available to the target tissue after administration. Many factors can affect bioavailability, including the dosage form and dissolution rate of the drug. Poor bioavailability is a significant problem encountered in the development of pharmaceutical compositions, particularly those containing an active ingredient that is poorly soluble in water. Poorly water soluble drugs tend to be eliminated from the gastrointestinal tract before being absorbed into the circulation of the patient. Moreover, poorly water soluble drugs tend to be unsafe for intravenous administration techniques, which are used primarily in conjunction with fully soluble drug substances.

As noted above, it is known that by increasing the surface area of a particulate drug, such as by decreasing the particle size of the drug, the rate of dissolution of the particulate drug is increased. Consequently, efforts have been made to control the size and size range of drug particles in pharmaceutical compositions and methods of making fine particulate drugs have been studied. For example, dry milling techniques have been used to reduce particle size and thereby influence drug absorption. However, in conventional dry milling, as discussed by Lachman et al., "The Theory and Practice of Industrial Pharmacy," *Milling*, 45 (1986), the limit of fineness is reached at about 100 microns (100,000 nm) when material cakes on the milling chamber. Lachman et al. also note that wet grinding is useful to further reduce particle size, but that flocculation restricts the lower particle size limit to approximately 10 microns (10,000 nm). Commercial airjet milling techniques have provided particles ranging in average particle size from as low as about 1 to 50 μm.

Other techniques for preparing pharmaceutical compositions to aid in dissolution and increase bioavailability include loading drugs into liposomes or polymers, such as during emulsion polymerization. However, such techniques exhibit problems and limitations. For example, a lipid soluble drug is often required in preparing suitable liposomes. Further, unacceptably large amounts of the liposomes or polymer are often required to prepare unit drug doses. Further still, techniques for preparing such pharmaceutical compositions tend to be complex.

One solution to the problem of preparing water-insoluble drugs previously suggested is to provide stable dispersible drug particles in the submicron size range, as described in U.S. Pat. No. 5,145,684 ("the '684 patent"), specifically incorporated herein by reference. The submicron sized particles can be prepared by wet milling in the presence of grinding media in conjunction with a surface stabilizer. Such particles can be readily prepared, do not appreciably flocculate or agglomerate due to interparticle attractive forces, and do not require the presence of a cross-linked matrix. In the '684 patent, the inventors hypothesized that the surface stabilizer hinders the flocculation and/or agglomeration of the drug particles by functioning as a mechanical or stearic barrier between the particles, thereby minimizing the close, interparticle approach necessary for agglomeration and flocculation. However, as noted in the '684 patent, not all stabilizers will function to produce a nanoparticulate composition of any drug.

Drug substances which have been difficult to formulate prior to the present invention because of their low solubility include HIV protease inhibitors, which are useful in the treatment of AIDS (acquired immune deficiency syndrome), caused by HIV infection.

AIDS was first recognized in 1981 as a clinical syndrome consisting of opportunistic infection and/or neoplasia associated with unexplained immunodeficiency. Shaw et al., *AIDS: Etiology, Diagnosis, Treatment, and Prevention*, 2nd Edition, DeVita, Jr. et al., eds., 11–31 (J. B. Lippincott Co., 1988). AIDS is a complex disease that includes progressive destruction of the immune system and degeneration of the central and peripheral nervous system. The discovery of HIV as the etiological agent of AIDS followed several years later. Id at 12–13.

HIV-1 and HIV-2 are retroviruses, and like all retroviruses, they have a RNA-dependent DNA polymerase. In the life cycle of the HIV virus, the cell-free virion first binds to the target cell. Following virus adsorption, reverse transcription catalyzed by the viral RNA-dependent DNA polymerase generates a double-stranded DNA copy of the single-strand viral RNA genome. Subsequent expression of viral DNA is controlled by a combination of viral and host cellular proteins interacting with viral DNA regulatory elements.

One method of treating HIV infection targets the reverse transcriptase (RT). Drugs which interfere with the HIV RT are nucleoside analogs, which include AZT (azidothymidine), ddI (didanosine), and ddT (dithiothreitol). However, such drugs are only modestly effective and are plagued by severe side effects because they interfere with cellular enzymes similar to the HIV viral enzyme they target.

An alternative method of treating HIV infection targets the HIV protease. The HIV protease, also known as proteinase, is essential for the final assembly of viable viral particles in HIV replication. Basically, the HIV protease cuts and trims the proteins that give the virus its structure. More specifically, the HIV protease cleaves a number of proteins from the viral Gag-Pol polyprotein precursor, including the HIV protease, the reverse transcriptase and integrase encoded in the pol gene, and the matrix, capsid, and nucleocapsid encoded in the gag gene. If the Gag-Pol precursor molecule is not processed in this way, noninfectious particles are formed. More importantly, HIV protease is unlike other enzymes in human cells and, therefore, inhibition of the HIV protease should not interfere with normal human cellular action. Inhibition of the HIV protease therefore represents an attractive treatment of HIV infection.

However, the identification of HIV protease inhibitors with antiretroviral activity in vivo has been hampered by the poor bioavailability of many molecules in this class. For example, it has been reported that the following HIV protease inhibitors, which are some of the largest and most complex drugs in development or marketed, all suffer from low oral bioavailability: Hoffmann La-Roche's saquinavir (INVIRASE®), Vertex's VX-478, Merck's MK-639 (L-735, 524) (also known as indinavir, and marketed under the trade name CRIXVAN®), Agouron Pharmaceutical's AG1343, Abbott Labs' ABT-538, Upjohn Co.'s U-103,017, Dupont Merck's DMP-450, and National Cancer Institute's and Japan Energy's KNI-272. *Early HIV Protease Inhibitors Difficult to Produce and Supplies Restricted,* Biotechnology Information Institute Antiviral Agents Bulletin, March, 1995. It has also been reported that many HIV protease inhibitors, such as saquinavir, are poorly soluble and therefore not very good at getting into the bloodstream. *Step By Step,* The Economist Newspaper, Nov. 26, 1994, at 93. Moreover, early trials of an HIV protease inhibitor developed by Searle were stopped because the drug seemed unable to enter the body's cells. Id With insolubility and low bioavailability, HIV protease inhibitors have to be given in huge doses to effect results. Id. For example, it has been reported that saquinavir is administered at 1800 mg/day, and indinavir (MK-639) is administered at 2400 mg/day, while the average amount of drug used to treat most diseases is 10–30 mg/day. Id. Thus, the dosage of a typical HIV protease inhibitor can be up to 24 times that of a typical drug. The low oral bioavailability and rapid biliary excretion of many HIV protease inhibitors have limited their utility as potential therapeutic agents. Thaisrivongs et al.,*J. Med. Chem.,* 39:2400–10 (1996). Such large dose requirements also translate to expensive drug protocols for patients.

HIV protease inhibitors have also been found to have an extremely poor taste. The poor taste, in conjunction with the necessity of large doses of the drugs, has made it extremely difficult, if not impossible, to develop formulations of the drugs which are palatable to patients. Even large doses of sweeteners have been unsuccessful in masking the unpleasant taste of the drugs.

There is a need in the art for compositions of HIV protease inhibitors which provide for high bioavailability and which are soluble in water. In addition, there is a need in the art for methods of making such compositions. The present invention satisfies these needs.

SUMMARY OF THE INVENTION

The present invention is directed to the surprising and unexpected discovery that the use of cellulosic surface stabilizers in nanoparticulate formulations of HIV protease inhibitors can form superior, stable, and dispersible compositions. This discovery is an improvement upon the invention described in U.S. Pat. No. 5,145,684.

It is an advantageous feature that the cellulosic surface stabilizers can be used to prepare nanoparticulate formulations of a wide range of HIV protease inhibitors.

In particular, the present invention comprises nanoparticulate HIV protease inhibitors having a cellulosic surface stabilizer adsorbed on the surface thereof in an amount sufficient to maintain an effective average particle size of less than about 1000, and more preferably, less than about 400 nm.

The invention also provides a stable dispersion comprising a liquid dispersion medium with the above-described nanoparticles dispersed therein. The terms "dispersion" or "suspension" are synonymous and used interchangeably herein and refer to a formulation in which the ingredient nanoparticles float undissolved in a fluid such as water.

In a preferred embodiment, a pharmaceutical composition is provided comprising the above-described nanoparticulate HIV protease inhibitor, a cellulosic surface stabilizer, and a pharmaceutically acceptable carrier therefor. The pharmaceutical compositions of the invention, which exhibit unexpectedly high bioavailability, may be formulated as a liquid, gel, solid, or any other appropriate formulation.

In another embodiment of the invention, there is provided a method of preparing the above-described nanoparticulate drug particles. The method comprises dispersing an HIV protease inhibitor in a liquid dispersion medium and applying mechanical means in the presence of grinding media to reduce the average particle size of the HIV protease inhibitor to an effective average particle size of less than about 1000 nm, and more preferably, less than about 400 nm. The drug particles can be reduced in size in the presence of a cellulosic surface stabilizer, or the drug particles can be contacted with a cellulosic surface stabilizer after attrition.

In yet another embodiment of the invention, a method for preparing a nanoparticulate pharmaceutical composition in a tablet form is provided. In such a method, the nanoparticles are compressed into tablets. The tablets generally also comprise at least one pharmaceutically acceptable carrier.

The present invention also provides for methods of treating mammals comprising administering to a mammal a pharmaceutical composition according to the invention, either alone or in combination with other treatments.

It is to be understood that both the foregoing general description and the following detailed description are exemplary and explanatory and are intended to provide further explanation of the invention as claimed. Other objects, advantages, and novel features will be readily apparent to those skilled in the art from the following detailed description of the invention.

DESCRIPTION OF THE PREFERRED EMBODIMENTS

The invention is directed to the unexpected discovery that nanoparticulate formulations of highly insoluble HIV protease inhibitors having an extremely small effective average particle size can be prepared using a cellulosic surface stabilizer. The nanoparticles are stable and do not appreciably flocculate or agglomerate due to interparticle attractive forces. In addition, such nanoparticles can be formulated into pharmaceutical compositions exhibiting unexpectedly high bioavailability.

The nanoparticles of the present invention comprise a drug substance as a discrete, crystalline phase. The crystalline phase differs from a non-crystalline or amorphous phase which results from precipitation techniques.

Poorly water soluble HIV protease inhibitor drug substances, many of which could not have been administered intravenously prior to the present invention, may be safely and effectively administered by intravenous methods in formulations according to the invention. Additionally, many HIV protease inhibitor drug substances which prior to the present invention could not have been administered orally due to poor bioavailability, may also be safely and effectively administered orally in formulations according to the present invention. Pharmaceutical compositions according to the present invention include the nanoparticles described above and a pharmaceutically acceptable carrier therefor. Suitable pharmaceutically acceptable carriers are well known to those skilled in the art and include, for example, non-toxic physiologically acceptable carriers, adjuvants, or vehicles for parenteral injection, for oral administration in solid or liquid form, for rectal administration, and the like.

Pharmaceutical compositions according to the present invention may also comprise binding agents, filling agents, lubricating agents, disintegrating agents, suspending agents, sweeteners, flavoring agents, preservatives, buffers, wetting agents, and other excipients. Examples of filling agents are lactose monohydrate, lactose hydrous, and various starches; examples of binding agents are various celluloses, preferably low-substituted hydroxylpropyl cellulose, and cross-linked polyvinylpyrrolidone; an example of a disintegrating agent is croscarmellose sodium; and examples of lubricating agents are talc, magnesium stearate, stearic acid, and silica gel. Examples of suspending agents are hydroxypropyl cellulose, methyl cellulose, hydroxyethyl cellulose, carboxymethyl cellulose sodium, hydroxypropyl methylcellulose, acacia, alginic acid, carrageenin, and other hydrocolloides. Examples of sweeteners are any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, such as orange, grape, cherry, berry, lemon-lime, and the like. Examples of preservatives, which control microbial contamination, are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

The pharmaceutical compositions according to the present invention are particularly useful in oral and parenteral, including intravenous, administration formulations. The pharmaceutical compositions may also be administered enterally. Examples of parenteral routes of administration include, but are not limited to, subcutaneous, intramuscular, respiratory, and intravenous injection, as well as nasopharyngeal, mucosal, and transdermal absorption. It is a particularly advantageous feature that the pharmaceutical compositions of the present invention exhibit unexpectedly high bioavailability, they provide more rapid onset of drug action, and they provide decreased gastrointestinal irritancy.

A method of treating a mammal in accordance with the present invention comprises the steps of administering to the mammal in need of treatment an effective amount of the nanoparticulate pharmaceutical composition described above. The selected dosage level of the drug substance for treatment is effective to obtain a desired therapeutic response for a particular composition and method of administration. The selected dosage depends, therefore, upon the particular drug substance, the desired therapeutic effect, the route of administration, the desired duration of treatment, and other factors. In addition, because the particle size of the drug has been dramatically reduced, the pharmaceutical composition of the present invention can comprise an identical dosage to a prior art large drug size dosage in a much smaller volume. Alternatively, the pharmaceutical composition of the present invention can deliver a smaller dosage as a greater percentage of the drug will be absorbed into the bloodstream of the patient as compared to prior art large drug size dosage. Both pharmaceutical compositions allow for greater camouflage of the poor taste of HIV protease inhibitors. The pharmaceutical compositions comprising the nanoparticulate drug substance are also useful in treatment of mammals in combination with other antivirals, immunomodulators, antibiotics, vaccines, or the like.

Description of Drug Substance

The HIV protease inhibitor drug substance is preferably present in an essentially pure form. In addition, the HIV protease inhibitor drug substance is poorly soluble, although it is dispersible in at least one liquid medium. By "poorly soluble" it is meant that the drug substance has a solubility in the liquid dispersion medium of less than about 10 mg/ml, and preferably less than about 1 mg/ml. A preferred liquid dispersion medium is water. However, the invention can be practiced with other liquid media in which the HIV protease inhibitor drug substance is poorly soluble and dispersible including, for example, aqueous salt solutions, safflower oil, and solvents such as ethanol, t-butanol, hexane, and glycol. The pH of the aqueous dispersion media can be adjusted by techniques known in the art.

Suitable HIV protease inhibitor drug substances can be selected from a variety of known drugs including but not limited to, for example, saquinavir, retinovir, VX-478, MK-639 (i.e, indinavir), AG1343, ABT-538, U-103,017, DMP-450, and KNI-272. The drug substances are commercially available and/or can be prepared by techniques known in the art.

As described below in the Examples, it has been discovered that stable and dispersible nanoparticulate formulations of HIV protease inhibitors can only be formed using cellulosic surface stabilizers, and that the use of other known surface stabilizers results in a composition which is not stable and dispersible. This discovery is significant in that, as noted above, the use of HIV protease inhibitors in the treatment of HIV infection has been limited prior to the present invention because of the low solubility and corresponding low bioavailability of the drugs. Moreover, the formation of nanoparticulate HIV protease inhibitor compositions enables the preparation of pharmaceutical compositions which are more palatable to patients. This is because as noted above, the use of a smaller volume, but the same dose, of drug allows for greater camouflage of the unpleasant taste of the HIV protease inhibitor using larger doses of sweeteners.

Pharmaceutically acceptable salts of the HIV protease inhibitor drug substance can also be used in the invention and include the conventional non-toxic salts or the quaternary ammonium salts which are formed, for example, from inorganic or organic acids or bases. Examples of such acid addition salts include, but are not limited to, acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxy-ethanesulfonate, lactate, maleate, methanesulfonate, 2-naphthalenesulfonate, nicotinate, oxalate, palmoate, pectinate, persulfate, 3-phenylpropionate, picrate, pivalate, propionate, succinate, tartrate, thiocyanate, tosylate, and undecanoate. Examples of base salts include, but are not limited to, ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and the like. In addition, the basic nitrogen-containing groups may be quaternized with such agents as lower alkyl halides, such as methyl, ethyl, propyl, and butyl chloride, bromides, and iodides; dialkyl sulfates such as dimethyl, diethyl, dibutyl, and diamyl sulfates; long chain halides such as decyl, lauryl, myristyl, and stearyl chlorides, bromides, and iodides; aralkyl halides such as benzyl and phenethyl bromides and the like. Other pharmaceutically acceptable salts include the sulfate salt ethanolate and sulfate salts.

Surface Stabilizer

The surface stabilizer of the present invention is a cellulosic stabilizer. Cellulosic surface stabilizers are non-ionic and water soluble. Examples of cellulosic stabilizers include, but are not limited to, hydroxypropyl cellulose (HPC), which is an ether of cellulose, HPC super low viscosity (HPC-SL), HPC-low viscosity (HPC-L), and hydroxypropyl methyl cellulose (HPMC).

The surface stabilizer is present at an amount of about 1 to about 100 mg/ml, preferably, about 10 mg/ml to about 20 mg/ml, and most preferably at about 10 mg/ml.

The cellulosic surface stabilizer can also be used in conjunction with one or more other surface stabilizers. Suitable additional surface stabilizers can preferably be selected from known organic and inorganic pharmaceutical excipients. Such excipients include various polymers, low molecular weight oligomers, natural products and surfactants. Preferred additional surface stabilizers include non-ionic and anionic surfactants. Representative examples of excipients include gelatin, casein, lecithin (phosphatides), gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropyl methycellulose phthalate, noncrystalline cellulose, magnesium aluminum silicate, triethanolamine, polyvinyl alcohol, and polyvinylpyrrolidone (PVP). Most of these excipients are described in detail in the *Handbook of Pharmaceutical Excipients,* published jointly by the American Pharmaceutical Association and The Pharmaceutical Society of Great Britain (The Pharmaceutical Press, 1986), the disclosure of which is hereby incorporated by reference in its entirety. The surface stabilizers are commercially available and/or can be prepared by techniques known in the art.

Particularly preferred surface stabilizers which can be used in conjunction with the cellulosic surface stabilizer, include polyvinyl pyrrolidone, Pluronic F68® and F108®, which are block copolymers of ethylene oxide and propylene oxide, Tetronic 908®, which is a tetrafunctional block copolymer derived from sequential addition of ethylene oxide and propylene oxide to ethylenediamine, dextran, lecithin, Aerosol OT®, which is a dioctyl ester of sodium sulfosuccinic acid, available from American Cyanamid, Duponol P®, which is a sodium lauryl sulfate, available from DuPont, Triton X-200®, which is an alkyl aryl polyether sulfonate, available from Rohm and Haas, Tween 80®, which is a polyoxyethylene sorbitan fatty acid ester, available from ICI Specialty Chemicals, and Carbowax 3350® and 934®, which are polyethylene glycols available from Union Carbide.

The nanoparticles of the invention contain a discrete phase of an HIV protease inhibitor drug substance with the cellulosic surface stabilizer adsorbed on the surface thereof. It has been discovered that the cellulosic surface stabilizer physically adheres to the drug substance, but it does not chemically bond to or chemically react with the drug. Such chemical bonding or interaction would be undesirable as it could result in altering the function of the drug. The surface stabilizer is adsorbed on the surface of the drug substance in an amount sufficient to maintain an effective average particle size of less than about 1000 nm, and more preferably, less than about 400 nm. Furthermore, the individually adsorbed molecules of the surface stabilizer are essentially free of intermolecular cross-linkages.

Quantities of Drug Substance and Surface Stabilizer

The relative amount of the HIV protease inhibitor drug substance and cellulosic surface stabilizer can vary widely. The optimal amount of the cellulosic surface stabilizer, and any other additional surface stabilizer, can depend upon, for example, the particular HIV protease inhibitor employed, the hydrophilic-lipophilic balance (HLB) of the stabilizer, the melting point and water solubility of the stabilizer, the surface tension of water solutions of the stabilizer, and the like.

The cellulosic surface stabilizer is preferably present in an amount of about 0.1 to about 10 mg per square meter of surface area of the drug substance, or in an amount of about 0.1 to about 90%, and more preferably about 20 to about 60% by weight based upon the total weight of the dry drug particle. Additional stabilizer, such as Aerosol OT®, in an amount of 0.01% to 1% by weight based upon the total weight of the dry particle are also preferable.

Reducing the Particle Size of the HIV Protease Inhibitor Drug Substance to Nanoparticles The nanoparticulate HIV protease inhibitor particles of the present invention can be prepared by first dispersing an HIV protease inhibitor in a liquid dispersion medium followed by applying mechanical means in the presence of grinding media to reduce the particle size of the drug substance to an effective average particle size of less than about 1000 nm, and more preferably, less than about 400 nm. The HIV protease inhibitor particles can be reduced in size in the presence of the cellulosic surface stabilizer or the drug particles can be contacted with the cellulosic surface stabilizer following attrition.

A general procedure for preparing the HIV protease inhibitor nanoparticles of the invention is set forth below. The HIV protease inhibitor is either obtained commercially or prepared by techniques known in the art in a conventional coarse form. It is preferred, but not essential, that the particle size of the selected drug be less than about 100 μm as determined by sieve analysis. If the coarse particle size of the drug is greater than about 100 μm, then it is preferred that the drug particles be reduced in size to less than about 100 μm using a conventional milling method, such as airjet or fragmentation milling, prior to reducing the particulate drug to submicron particle size.

The coarse HIV protease inhibitor particles can then be added to a liquid medium in which the drug is essentially insoluble to form a premix. The concentration of the drug in the liquid medium can vary from about 0.1 to about 60%, but is preferably from about 5 to about 30% (w/w). It is preferred, but not essential, that the cellulosic surface stabilizer is present in the premix. The concentration of the cellulosic surface stabilizer can vary from about 0.1 to about 90%, but it is preferably from about 1 to about 75%, and more preferably from about 20 to about 60%, by weight based upon the total combined weight of the HIV protease inhibitor and surface stabilizer. The apparent viscosity of the premix suspension is preferably less than about 1000 centipoise.

The premix can be used directly by subjecting it to mechanical means to reduce the average particle size in the dispersion to less than about 1000 nm, and more preferably, less than about 400 nm. It is preferred that the premix be used directly when a ball mill is used for attrition. Alternatively, the HIV protease inhibitor, and optionally the cellulosic surface stabilizer, can be dispersed in the liquid medium using suitable agitation, such as a roller mill or a Cowles-type mixer, until a homogeneous dispersion is observed. In a homogeneous dispersion, no large agglomerates are visible to the naked eye. It is preferred that the premix be subjected to such a premilling dispersion step when a recirculating media mill is used for attrition.

The mechanical means applied to reduce the particle size of the HIV protease inhibitor can be a dispersion mill. Suitable dispersion mills include, but are not limited to, a ball mill, an attritor mill, a vibratory mill, and media mills such as a sand mill or a bead mill. A media mill is preferred due to the relatively shorter milling time required to provide the desired reduction in particle size. For media milling, the apparent viscosity of the premix is preferably from about 100 to about 1000 centipoise. For ball milling, the apparent viscosity of the premix is preferably from about 1 to about 100 centipoise. Such ranges tend to afford an optimal balance between efficient particle fragmentation and media erosion.

The attrition time can vary widely and depends primarily upon the particular mechanical means and processing conditions selected. For ball mills, processing times of up to five days or longer may be required. Using a high shear media mill, processing times of less than 1 day (residence times of from one minute up to several hours) have provided the desired results.

The HIV protease inhibitor particles must be reduced in size at a temperature which does not significantly degrade the drug substance. Processing temperatures of less than about 30–40° C. are ordinarily preferred. If desired, the processing equipment can be cooled with conventional cooling equipment. Generally, the methods of the invention can be conveniently carried out under conditions of ambient temperature and at processing pressures which are safe and effective for the milling process. For example, ambient processing pressures are typical of ball mills, attritor mills, and vibratory mills. Control of the temperature, for example, by jacketing or immersion of the milling chamber in ice water, is encompassed by the invention.

Processing pressures from about 1 psi (0.07 kg/cm$^2$) up to about 50 psi (3.5 kg/cm$^2$) are encompassed by the invention. Processing pressures typically range from about 10 psi to about 20 psi.

The surface stabilizer, if not present in the premix, must be added to the dispersion after attrition in an amount as described for the premix above. Thereafter, the dispersion can be mixed by, for example, shaking vigorously. Optionally, the dispersion can be subjected to a sonication step using, for example, an ultrasonic power supply. In such a method, the ultrasonic power supply can, for example, release ultrasonic energy having a frequency of about 20 to about 80 kHz for a time of about 1 to about 120 seconds.

After attrition is completed, the grinding media is separated from the milled particulate product using conventional separation techniques, such as by filtration, sieving through a mesh screen, and the like. The surface stabilizer may be added to the milled particulate product either before or after the milled product is separated from the grinding media In a preferred grinding process, the particles are made continuously. In such a continuous method, the slurry of HIV protease inhibitor/cellulosic surface stabilizer and optionally an additional surface stabilizer is continuously introduced into a milling chamber, the HIV protease inhibitor is continuously contacted with grinding media while in the chamber to reduce the particle size of the HIV protease inhibitor, and the HIV protease inhibitor is continuously removed from the milling chamber. The cellulosic surface stabilizer, either alone or in conjunction with one or more additional surface stabilizers, can also be continuously added to the media chamber along with the HIV protease inhibitor, or it can be added to the HIV protease inhibitor which is removed from the chamber following grinding.

The resulting dispersion of the present invention is stable and comprises the liquid dispersion medium described above. The dispersion of surface stabilizer and nanoparticulate HIV protease inhibitor can be spray dried, spray coated onto sugar spheres or onto a pharmaceutical excipient using techniques well known in the art.

Grinding Media

The grinding media for the particle size reduction step can be selected from rigid media which is preferably spherical or particulate in form and which has an average size of less than about 3 mm and, more preferably, less than about 1 mm. Such media can provide the desired drug particles of the invention with shorter processing times and impart less wear to the milling equipment. The selection of material for the grinding media is not believed to be critical. Zirconium oxide, such as 95% ZrO stabilized with yttrium and 95% ZrO stabilized with magnesia, zirconium silicate, and glass grinding media have been found to provide particles having acceptable minimal levels of contamination for the preparation of pharmaceutical compositions. Other media, such as stainless steel, titania, and alumina can also be used. Preferred grinding media have a density greater than about 3 g/cm$^3$.

Polymeric Grinding Media

The grinding media can comprise particles, preferably spherical in shape, such as beads, consisting of essentially polymeric resin. Alternatively, the grinding media can comprise particles having a core with a coating of the polymeric resin adhered thereto. The media can range in size from about 0.1 to about 3 mm. For fine grinding, the particles preferably are from about 0.2 to about 2 mm, and more preferably, from about 0.25 to about 1 mm in size.

The polymeric resin can have a density from about 0.8 to about 3.0 g/cm$^3$. Higher density resins are preferred as such resins can provide more efficient particle size reduction.

In general, polymeric resins suitable for use in the present invention are chemically and physically inert, substantially free of metals, solvent, and monomers, and of sufficient hardness and friability to enable them to avoid being chipped or crushed during grinding. Suitable polymeric resins include, but are not limited to, cross-linked polystyrenes, such as polystyrene cross-linked with divinylbenzene, styrene copolymers, polycarbonates, polyacetals such as Delrin®, vinyl chloride polymers and copolymers, polyurethanes, polyamides, poly (tetrafluoroethylenes), such as Teflon® and other fluoropolymers, high density polyethylenes, polypropylenes, cellulose ethers and esters such as cellulose acetate, polyhydroxymethacrylate, polyhydroxyethyl acrylate, silicone containing polymers such as polysiloxanes, and the like. The polymer can also be biodegradable. Exemplary biodegradabe polymers include, but are not limited to, poly(lactides), poly(glycolide) copolymers of lactides and glycolide, polyanhydrides, poly (hydroxyethyl methacrylate), poly(imino carbonates), poly (N-acylhydroxyproline)esters, poly(N-palmitoyl hydroxyproline) esters, ethylene-vinyl acetate copolymers, poly(orthoesters), poly(caprolactones), and poly (phoshazenes). For biodegradable polymers, contamination of the resultant composition from the media itself can advantageously metabolize in vivo into biologically acceptable products that can be eliminated from the body.

The grinding media is separated from the milled particulate HIV protease inhibitor using conventional separation techniques in a secondary process, such as by filtration, sieving through a mesh filter or screen, and the like. Other separation techniques such as centrifugation may also be employed.

Particle Size

As used herein, particle size is determined on the basis of the average particle size as measured by conventional techniques well known to those skilled in the art, such as sedimentation field flow fractionation, photon correlation spectroscopy, or disk centrifugation. When photon correlation spectroscopy (PCS) is used as the method of particle sizing, the average particle diameter is the Z-average particle diameter known to those skilled in the art. By "an average effective particle size of less than about 1000 mm," it is meant that at least 90% of the particles, by weight, have a particle size of less than about 1000 nm when measured by the above-noted techniques. In a preferred embodiment of the invention, the effective average particle size is less than about 400 nm, more preferred is less than about 250 nm, and in an even more preferred embodiment, the effective average particle size is less than about 100 nm. It is preferred that at least 95% and, more preferably, at least 99% of the particles have a particle size less than the effective average, e.g., 1000 nm. In a particularly preferred embodiment, essentially all of the particles have a size of less than about 400 nm, in a more preferred embodiment, essentially all of the particles have a size of less than about 250 nm, and in a most preferred embodiment, essentially all of the particles have a size of less than about 100 nm.

Preparing Tablet Formulations

An exemplary process for preparing nanoparticulate HIV protease inhibitors in a tablet formulation comprises: (1) using the method described below to obtain spray-dried nanoparticles of the drug substance; (2) sieve-screening the spray-dried nanoparticles to obtain uniform particles of less than about 20 mesh; (3) blending the nanoparticulate drug substance with tableting excipients; (4) compressing the uniform particles into tablets using a tableting apparatus; and (5) film coating the tablets.

The spray drying process is used to obtain an "intermediate" nanoparticulate powder subsequent to the milling process used to transform the HIV protease inhibitor into nanoparticles. In an exemplary spray drying process, the high-solids drug substance nanosuspension and the cellulosic surface stabilizer are fed to an atomizer using a peristatic pump and atomized into a fine spray of droplets. The spray is contacted with hot air in the drying chamber resulting in the evaporation of moisture from the droplets. The resulting spray is passed into a cyclone where the powder is separated and collected.

At the completion of the spray drying process, the collected spray-dried intermediate comprises the nanoparticles of the HIV protease inhibitor suspended in a solid polymer matrix of the cellulosic surface stabilizer. The moisture content of the intermediate is controlled by the operating conditions of the spray drying process. The characteristics of the nanoparticulate powder are critical to the development of a free flowing powder that can be blended with other excipients suitable for a directly compressible tablet formulation.

Tablets can be made using a direct compression tablet process or using a roller compaction process. In an exemplary direct compression process, the spray-dried intermediate and stabilizer are sieved through a screen and the screened material is blended. The desired excipients are sieved and added to the blender. At the completion of blending, the contents of the blender can be discharged into a tared collection container and compression of tablet cores can be completed on a tablet press. The blended material can be fed into a feed hopper and force-fed into the die cavities using an automatic feeder. The tablet press operating conditions can be set to meet thickness, hardness, and weight specifications. Upon completion of the compression operation, a film-coating can be applied to the tablet cores using, for example, a Vector-Freund Hi-Coater machine.

In an exemplary roller compaction process following the media milling process, the nanoparticulate HIV protease inhibitor suspension can be spray dried to form an intermediate. The spray dryer can be assembled in a co-current configuration using a rotary atomization nozzle and the nanosuspension can be fed to the rotary atomizer using a peristaltic pump. Acceptable spray-dried product has a moisture content which does not exceed 1.0% (w/w).

A dry granulation operation can be used to manufacture tablets comprising the HIV protease inhibitor drug substance. Required amounts of the HIV protease inhibitor drug substance/cellulosic surface stabilizer spray-dried intermediate and appropriate excipients can be screened and blended. The blended material is then compacted using, for example, a roller compactor. The compacted material can then be granulated. Following granulation, additional excipients can be screened and blended with the granulation. The blended materials can then be compressed into tablets using a tablet press followed by coating.

Process Flow Diagram A show a process of manufacturing tablets by direct compression, and Process Flow Diagram B shows a process of manufacturing tablets by roller compaction.

PROCESS FLOW DIAGRAM - A
Direct Compression

Pre-Mix
⇓
Media Mill
⇓
Spray Dry
⇓
Screen/Sieve
⇓
Blend
⇓
Compress
⇓
Film Coat

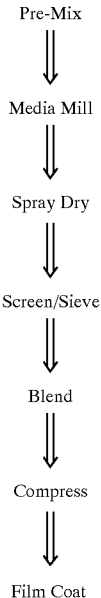

PROCESS FLOW DIAGRAM - B
Roller Compaction

Pre-Mix
⇓
Media Mill
⇓
Spray Dry
⇓
Blend
⇓
Roll Compact
⇓
Granulate
⇓
Sieve
⇓
Blend
⇓
Granulate
⇓

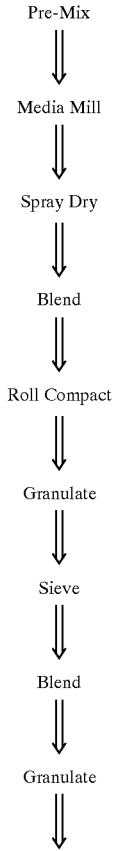

Tablet
⇓
Coat

The following examples are given to illustrate the present invention. It should be understood, however, that the invention is not to be limited to the specific conditions or details described in these examples.

Examples 1–7 describe the formation of nanoparticulate compositions of indinavir.

EXAMPLE 1

The purpose of this example was to demonstrate the formation of a nanoparticulate composition of indinavir, the sulphate salt of which is marketed as CRIXIVAN® (trademark of Merck & Co., Inc.), i.e., indinavir sulfate. Indinavir, or N-(2-(R)-hydroxy-1(S)-indanyl)-2(R)-phenylmethyl-4-(S)-hydroxy-5-(1 -(4-(3-pyridylmethyl)-2(S)-N'-(t-butylcarboxamido)-piperazinyl))-pentaneamide, is a HIV protease inhibitor useful in treating AIDS and ARC (AIDS Related Complex). Indinavir can be chemically synthesized using techniques known in the art, and it is commercially available from Merck & Co., Inc., Rahway, N.J.

A surface stabilizer solution comprising 90 ml 2.5% (w/w) of HPC-SL in purified water was added into a 500 ml Pyrex® roller mill bottle. 10% (w/w, 10.0 g) of the indinavir was dispensed incrementally into the HPC-SL stabilizer solution until the entire amount was added. 250 ml of 0.5 mm YTZP media (Yttria doped Zirconia beads commercially available from Toray, Japan) was charged into the 500 ml roller mill bottle. The bottle was placed on a roller mill (U.S. Stoneware, Akron, Ohio) with the roller speed set at 160 rpm and milled for 4 days.

A sample of the indinavir/HPC-SL slurry was removed and analyzed for particle size. The particle size of the sample was measured with a Microtrack UPA sizer according to the following procedures. First, the chamber of the instrument was rinsed three times with DI water. Next, the chamber was filled with 50 ppm DOSS (dioctyl sodium sulfosuccinate) and one drop of 204 nm standard was placed into the chamber. Using a disposable transfer pipette, the contents of the chamber were gently agitated for ten seconds. The signal level was checked to be within 0.2–0.3 (unitless). If the level was higher, the sample was diluted by removing some of the contents in the chamber and adding DOSS solution. Once the sample was in the signal level range, it was run by selecting "run w/o save" for 180 seconds. The chamber of the instrument was then rinsed three times and filled with 50 ppm DOSS solution. A sample of the nanoformulation to be tested was added carefully into the DOSS solution in the chamber to gradually increase the signal level to within 0.2–0.3 (unitless). Once the sample was in the signal level range, it was run for 180 seconds to determine the size of the particle. The chamber of the instrument was then rind three times and filled with 50 ppm DOSS solution in preparation for the next test.

It was determined that the mean size of the indinavir/HPC-SL nanoparticles was 186 nm.

EXAMPLE 2

The purpose of this example was to demonstrate the formation of a nanoparticulate composition of indinavir.

A surface stabilizer solution comprising 90 ml 3.30% (w/w) of HPC-SL in purified water was added into each of four 500 ml Pyrex® roller mill bottles. 10% (w/w, 10.0 g) of the indinavir was dispensed incrementally into the HPC-SL stabilizer solution until the entire amount was added and the solution appeared mixed. 250 ml of 0.5 mm YTZP media (Yttria doped Zirconia beads commercially available from Toray, Japan) was charged into each of the four 500 ml Pyrex roller mill bottles. The bottles were placed on a roller mill (U.S. Stoneware, Akron, Ohio) with the roller speed set at 160 rpm and milled for 5 days.

Following particle size analysis, it was determined that the mean size of the indinavir/HPC-SL nanoparticles was 142 nm–152 nm.

EXAMPLE 3

The purpose of this example was to demonstrate the formation of a nanoparticulate composition of indinavir.

A surface stabilizer solution comprising 13.5 g 3.73% (w/w) of HPC-SL in purified water was added into a 60 ml roller mill bottle. 10% (w/w, 1.5 g) of the indinavir was dispensed incrementally into the HPC-SL surface stabilizer solution until the entire amount was added. 30 ml of 0.5 mm YTZP media (Yttria doped Zirconia beads commercially available from Toray, Japan) was charged into the 60 ml roller mill bottle. The bottle was placed on a roller mill (U.S. Stoneware, Akron, Ohio) with the roller speed set at 160 rpm and milled for 9 days.

Following particle size analysis, it was determined that the mean size of the indinavir/HPC-SL nanoparticles was 267 nm.

EXAMPLE 4

The purpose of this example was to demonstrate the formation of a nanoparticulate composition of indinavir.

A surface stabilizer solution comprising 2.75 ml 1.0% (w/w) of HPC-SL in purified water was added into a 15 ml roller mill bottle. 2% (w/w, 75 mg) of the indinavir was dispensed incrementally into the HPC-SL surface stabilizer solution until the entire amount was added. 7.5 ml of 0.5 mm YTZP media (Yttria doped Zirconia beads commercially available from Toray, Japan) was charged into the 15 ml roller mill bottle. The bottle was placed on a roller mill (U.S. Stoneware, Akron, Ohio) with the roller speed set at 160 rpm and milled for 12 days.

Following particle size analysis, it was determined that the mean size of the indinavir/HPC-SL nanoparticles was 127 nm.

EXAMPLE 5

The purpose of this example was to demonstrate the formation of a nanoparticulate composition of indinavir.

A surface stabilizer solution comprising 118.25 g 1.07% (w/w) of HPC-SL in purified water was added into a 500 ml Pyrex® roller mill bottle. 5% (w/w, 6.25 g) of the indinavir was dispensed incrementally into the HPC-SL surface stabilizer solution until the entire amount was added. 250 ml of 0.5 mm YTZP media (Yttria doped Zirconia beads commercially available from Toray, Japan) was charged into the 500 ml roller mill bottle. The bottle was placed on a roller mill (U.S. Stoneware, Akron, Ohio) with the roller speed set at 160 rpm and milled for 5 days.

Following particle size analysis, it was determined that the mean size of the indinavir/HPC-SL nanoparticles was 172 nm.

EXAMPLE 6

The purpose of this example was to demonstrate the formation of a nanoparticulate composition of indinavir.

A surface stabilizer solution comprising 3.75 ml 1.0% (w/w) of HPMC in purified water was added into a 15 ml roller mill bottle. 2% (w/w) of the indinavir was dispensed incrementally into the HPMC surface stabilizer solution until the entire amount was added. 7.5 ml of 0.5 mm YTZP media (Yttria doped Zirconia beads commercially available from Toray, Japan) was charged into the 15 ml roller mill bottle. The bottle was placed on a roller mill (U.S. Stoneware, Akron, Ohio) with the roller speed set at 160 rpm and milled for 12 days.

Following particle size analysis, it was determined that the mean size of the indinavir/HPMC nanoparticles was 240 nm.

EXAMPLE 7

The purpose of this example was to demonstrate the use of high energy milling to provide a nanoparticulate composition of indinavir at higher than 30% w/w.

A Dyno Mill (Type KDL, cat. # 6094-AEA) was used in the size reduction process. 510 ml of 500 $\mu$m SDy20 polymeric media were added into a 600 ml milling chamber. An agitator composed of four 64 mm diameter polyblades and a shaft rotation of 2500 rpm was used in the milling process. DI water was used to cool the seal and the milling chamber. DI water at 4° C. was circulated through the jacketed milling chamber and the seals of the mill during the milling operation.

The size reduction process was performed in a recirculation mode. Suspension or slurry was pumped at a flow rate of 150 ml/min from a 1.5 L jacketed holding tank into the milling chamber and back out into the holding tank.

Added to the holding tank were 323.19 gm of indinavir, 31.42 gm of HPC-SL, and 1277 gm of diluent, which comprised of xylitol at 151 mg/ml, Magnasweet® at 3.05 mg/ml, Tween 80® at 0.57 mg/ml, sodium citrate at 1.67 mg/ml, orange flavor at 10.1 mg/ml, potassium sorbate at 3.26 mg/ml, methylparaben at 0.76 mg/ml, propylparaben at 0.076 mg/ml, and water at 880 mg/ml, with the pH adjusted to 7.0 using 0.1 N NaOH. The ingredients inside the holding tank were cooled by circulating DI water at 4° C. through the jacket. A Servo Dyne mixer was inserted into the holding tank for 1 hour to dissolve the HPC-SL and to wet the drug powder. The slurry was then pumped into the Dyno mill chamber with a peristaltic pump at a flow rate of 150 ml/min. After the milling chamber was filled, the Dyno mill was turned on and the suspension was milled in the recirculation mode for 2½ hours to provide an indinavir nanocrystalle suspension at a pH of 7.68. The particle size of the harvested indinavir formulation was 50% at 100 nm and 90% at 147 nm when measured with a Horiba LA910 instrument, and it was 50% at 157 nm and 90% at 231 nm when measured with a Microtrack UPA instrument.

Examples 8–12 are directed to the formation of nanoparticulate compositions of VX478, a HIV protease inhibitor.

EXAMPLE 8

The purpose of this example was to demonstrate the formation of a nanoparticulate composition of VX478, which is a HIV protease inhibitor, using Dyno milling. VX-478 is commercially available from Vertex Pharmaceuticals, Inc., Cambridge, Mass., and methods of making VX-478 are described in U.S. Pat. No. 5,585,397.

A Dyno Mill (Type KDL cat. # 6094-AEA) was used in the process. A 300 ml milling chamber containing 240 ml of 500 µm SDy20 polymeric media and an agitator composed of two 64 mm diameter polyblades having a shaft rotation of 2500 rpm were used in the milling process. DI water at 4° C. was circulated through the jacketed milling chamber and the seals of the mill during the size reduction process.

The size reduction process was done in a recirculation mode. Suspension or slurry was pumped at a flow rate of 150 ml/min from a jacketed holding tank (1.5 liter) into the milling chamber and back out into the holding tank. 120 gm of VX478, 18 g of HPC-L, 60 mg of DOSS, and 500 ml of WFI were added to the holding tank. The ingredients inside the holding tank were cooled by circulating DI water at 4° C. through the jacket. A Servo Dyne mixer was inserted into the holding tank for 1 hour to dissolve the HPC-L and DOSS and to wet the drug powder. The slurry was then pumped into the Dyno mill chamber with a peristaltic pump at a flow rate of 157 ml/min. After the milling chamber was filled, the Dyno mill was turned on and the suspension was milled in the recirculation mode for 4 hours to provide a VX478 nanocrystalline suspension at a pH of 6. The particle size of the harvested VX478 formulation was 50% at 169 nm and 90% at 221 nm when measured with a Horiba LA910 instrument.

EXAMPLE 9

The purpose of this example was to demonstrate the formation of a dry film nanoparticulate composition of VX-478.

A VX-478 nanoparticulate formulation as prepared in Example 84 was mixed with sugar (preferably sucrose or mannose), HPC-L, DOSS, and WFI to provide a suspension with the drug:sugar ratio preferably between 5:3 and 14:10.

The thoroughly mixed suspension was distributed into Teflon® containers covering ⅛ of an inch in height. The suspension was then allowed to dry under clean air to afford the dried film. The dried film was resuspended in WFI or SGF to provide a nanocrystalle suspension with a 50% particle size between 180 nm to 200 nm and a 90% size between 250 nm to 300 nm when measured with a Horiba LA910 instrument.

EXAMPLE 10

The purpose of this example was to demonstrate the formation of a nanoparticulate composition of VX478.

A stock surface stabilizer solution consisting of 2.5% (w/v) HPC-L (Nisso DI-0031) was prepared in distilled water. A 15 mL polycarbonate mini-DC milling tube was charged with 2.5 mL (1.625 grams) of 0.5 mm Sdy-20 polymeric milling media Approximately 2.5 mL of a 1.0% (w/v) VX478/1.0% (w/v) HPC-L/water slurry was prepared directly in the DC milling tube by combining the following ingredients:

0.025 grams VX478

1.0 mL stock HPC-L stabilizer solution (@ 2.5% w/v)

1.5 mL water

The mini-DC milling tube was water jacketed and cooled with tap water. The slurry and media were milled for 5 hours using a mini-DC mill stainless steel shaft at a milling speed of 2000 rpm.

The dispersion settled upon standing overnight but was easily resuspended. The particle size was measured using a Horiba LA 900 Particle Size Analyzer, with a limited volume fraction cell, 0.2 µm filtered 0.01% DOSS as the sizing diluent, and a sonication time of 30 seconds. The mean particle size was 582 nm with 90% of the particles having a particle size of less than 880 nm. The nanosuspension was stable in SGF and SIF. After 13 days storage at ambient room temperature the nanosuspension had a mean particle size of 571 nm with 90% of the particles having a particle size of less than 830 nm.

EXAMPLE 11

The purpose of this example was to demonstrate the formation of a nanoparticulate composition of VX478.

A stock surface stabilizer solution consisting of 2.5% (w/w) HPC-L (Nisso DI-0031) was prepared in distilled water. A stock stabilizer solution of 1.0% (w/w) SDS was prepared in distilled water. A 100 mL polycarbonate DC milling tube was charged with 10.0 mL (6.5 grams) of 0.5 mm Sdy20 polymeric milling media. Approximately 10 grams of a 2.0% (w/w) VX478/1.0% (w/w) HPC-L/water slurry was prepared directly in the DC milling tube by combining the following ingredients:

0.20 grams VX478

4.0 grams stock HPC-L stabilizer solution (@ 2.5% w/w)

5.8 grams water

The DC milling tube was water jacketed and cooled with tap water. The slurry and media were milled for 4 hours using a standard size, tefzel-coated DC milling shaft at a milling speed of 2300 rpm.

Following the completion of the milling process, the dispersion was separated from the media by filtering through a stainless steel mesh syringe filter. The mass of the collected dispersion was calculated and an appropriate amount of 1.0% (w/w) SDS was added such that the concentration of SLS in the final dispersion was 0.01% (w/w). (The SDS was added because it was found that upon scaling up to a 2:1 concentration in the standard DC mill, the dispersion formed loose agglomerates that were visualized microscopically, but which were not represented on the particle size distributions due to the sonication step during the size measurement process. Addition of SDS to a final concentration of 0.01% prevented the formation of the loose agglomerates.) The VX478/HPC-L/SDS composition was mixed well and the particle size, fluid stability, and shelf stability were determined.

The particle size was measured using a Horiba LA 900 Particle Size Analyzer, with a limited volume fraction cell, 0.2 µm filtered 0.01% DOSS as the sizing diluent, and a sonication time of 30 seconds. The mean particle size was 230 nm with 90% of the particles having a particle size of less than 315 nm. The nanosuspension was stable when mixed 1:1 with SGF and SIF. After 14 days storage at ambient room temperature the nanosuspension had a mean particle size of 268 nm with 90% of the particles having a particle size of less than 384 nm.

In a repetition of this experiment, the nanosuspension had a mean particle size of 157 nm with 90% of the particles having a particle size of less than 300 nm.

EXAMPLE 12

The purpose of this example is to summarize surface stabilizers and size reduction techniques which are inadequate or insufficient to produce a nanoparticulate composition of VX478.

Procedures: Stock surface stabilizer solutions consisting of 2.5% (w/v) PVP K-29/32, 2.5% (w/v) Pluronic F68®, 2.5% (w/v) Pharmacoat 603®, 2.5% (w/v) Methocel K100LV®, and 2.5% (w/v) Pluronic F108® were prepared in distilled water.

Five 15 mL polycarbonate mini-DC milling tubes were charged with 2.5 mL (1.625 grams) each of 0.5 mm Sdy20 polymeric milling media. Approximately 2.5 mL of a 1.0% (w/v) VX478/1.0% (w/v) stabilizer/water slurry was prepared directly in each of the DC milling tubes by combining the following ingredients:

0.025 grams VX478

1.0 mL stock stabilizer solution (@ 2.5% w/v)

1.5 mL water

The mini-DC milling tubes were water jacketed and cooled with tap water. The slurry and media were milled for various time intervals using mini-DC mill stainless steel shafts at a milling speeds of 2000 rpm.

a) 1.0% VX478 in 1.0% PVP K-29/32®: Following 8 hours of DC milling, the resultant mixture contained unmilled drug and agglomerates. No size reduction was observed. 3.75 mL of an identical slurry preparation was also roller milled in a 15 mL bottle with 7.5 mL of 0.5 mm YTZ media After 3 days, unmilled drug with no size reduction was observed. The particle size was measured using a Horiba LA 900 Particle Size Analyzer, with a limited volume fraction cell, 0.2 μm filtered 0.01% DOSS as the sizing diluent, and a sonication time of 30 seconds. The mean particle size was measured to be greater than 7 μm.

b) 1.0% VX478 in 1.0% Pluronic F68®: Following 4 hours of DC milling, the resultant mixture contained unmilled drug and no size reduction was observed. The particle size was measured as described in subsection (1) above. The mean particle size was measured to be greater than 20 μm.

c) 1.0% VX478 in 1.0% Pharmacoat 603®: Following 4 hours of DC milling, the resultant mixture contained large, tight agglomerates. The particle size was measured as described in subsection (1) above. The mean particle size was measured to be approximately 400 nm (agglomerates broken during sonication). The size distribution had a long tail extending beyond 10 μm.

d) 1.0% VX478 in 1.0% Methocel K100LV®: Following milling for 11 hours, the resultant mixture had a mean particle size of 302 nm with 90% of the particles having a particle size of less than 408 nm. The particle size was measured as described in subsection (1) above. When this dispersion was scaled up to a 2:1 concentration ratio in a standard size DC mill, excessive foaming was encountered, although an acceptable particle size was obtained (Mean size of 297 nm, 90% less than 400 nm). After 3 days on the shelf, a peak possibly representing large agglomerates appeared during the size measurement indicating potential shelf instability of the nanosuspension.

e) 1.0% VX478 in 1.0% Pluronic F108®: Following milling for 8 hours, the resultant suspension had a mean particle size of 400 nm, with 90% of the particles having a size of less than 530 nm. After 3 days, the nanosuspension had a mean particle size of 375 nm, with 90% of the particles having a size of less than 490 nm. The particle sizes were measured as described in subsection (1) above. The nanosuspension was stable in the presence of SGF and SIF. When this dispersion was scaled to a 2:1 concentration in a standard DC mill, excessive foaming was encountered, the drug substance was difficult to wet into the stabilizer phase, and the dispersion quickly settled.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

We claim:

1. A method of treating Human Immunodeficiency Virus (HIV) in a mammal comprising administering to the mammal an effective amount of a pharmaceutical composition comprising:

(a) a crystalline HIV protease inhibitor having a solubility in water of less than about 10 mg/ml, and (b) a cellulosic surface stabilizer adsorbed on to the surface of the HIV protease inhibitor in an amount sufficient to maintain an effective average particle size of less than about 1000 nm, and a pharmaceutically acceptable carrier therefor.

2. The method of claim 1, wherein the surface stabilizer is selected from the group consisting of HPC, HPMC, HPC-SL, and HPC-L.

3. The method of claim 1, wherein the particles have an effective average particle size of less than about 400 nm.

4. The method of claim 3, wherein the particles have an effective average particle size of less than about 250 nm.

5. The method of claim 4, wherein the particles have an effective average particle size of less than about 100 nm.

6. The method of claim 1, wherein the nanoparticles have at least one additional surface stabilizer adsorbed to the surface of the HIV protease inhibitor.

7. The method of claim 1, wherein the HIV protease inhibitor is selected from the group consisting of saquinavir, retinovir, VX-478, AG1343, ABT-538, U-103,017, DMP-450, and KNI-272.

8. The method of claim 1, wherein said composition is administered via a method selected from the group consisting of orally, parenterally, and enterally.

9. The method of claim 8, wherein the parenteral route of administration is selected from the group consisting of subcutaneously, intramuscularly, via the respiratory system, intravenously, nasopharylngeally, mucosally, and transdermally.

10. The method of claim 1, wherein the composition is in a solid dosage form.

11. The method of claim 1, wherein said composition is a liquid dispersion of the HIV protease inhibitor/cellulosic surface stabilizer particles.

12. The method of claim 11, wherein said the dispersion medium of the dispersion is selected from the group consisting of water, salt solutions, and safflower oil.

13. The method of claim 1, wherein the mammal is concurrently treated with another therapy for HIV infection.

* * * * *